United States Patent
Chen et al.

(10) Patent No.: US 7,116,815 B2
(45) Date of Patent: Oct. 3, 2006

(54) CHROME-LESS MASK INSPECTION METHOD

(75) Inventors: Ming-Jui Chen, Hsinchu (TW); Chin-Lung Lin, Hsinchu Hsien (TW)

(73) Assignee: United Microelectronics Corp., Hsinchu (TW)

( * ) Notice: Subject to any disclaimer, the term of this patent is extended or adjusted under 35 U.S.C. 154(b) by 697 days.

(21) Appl. No.: 10/435,566

(22) Filed: May 9, 2003

(65) Prior Publication Data
US 2004/0218805 A1    Nov. 4, 2004

(30) Foreign Application Priority Data
May 2, 2003    (TW) ............................. 092112090

(51) Int. Cl.
*G06K 9/00* (2006.01)

(52) U.S. Cl. ............... 382/144; 382/145; 382/149; 356/237.4; 250/559.45; 430/5

(58) Field of Classification Search .......... 382/144, 382/145, 147, 149, 305; 250/310, 559.45, 250/307, 397, 306; 356/237.4, 237.1, 73; 430/5, 30, 311, 322
See application file for complete search history.

(56) References Cited

U.S. PATENT DOCUMENTS

| | | | |
|---|---|---|---|
| 6,221,538 B1 * | 4/2001 | Kerszykowski et al. | 430/5 |
| 6,388,736 B1 * | 5/2002 | Smith et al. | 355/53 |
| 6,396,944 B1 * | 5/2002 | Kung | 382/144 |
| 6,541,167 B1 * | 4/2003 | Petersen et al. | 430/5 |
| 6,986,972 B1 * | 1/2006 | Rissman | 430/5 |

\* cited by examiner

*Primary Examiner*—Sheela Chawan
(74) *Attorney, Agent, or Firm*—J.C. Patents

(57) ABSTRACT

A chrome-less mask inspection method is provided. The chrome-less mask at least includes a transparent region and a phase shift region. The method includes providing a database having a mask database corresponding to the chrome-less mask. The mask database further includes a frame line pattern having enclosed area and pattern that corresponds to enclosed area and pattern of the phase shift region of the chrome-less mask and a first inspection signal pattern generated by the mask database. An inspecting device is also provided to inspect a second inspection signal pattern from the chrome-less mask. Furthermore, scanning location of the second inspection signal pattern corresponds with scanning location of the first inspection signal pattern. Thereafter, the first inspection signal pattern and the second inspection signal pattern is compared and any differences are registered.

12 Claims, 10 Drawing Sheets

CHROME-LESS MASK INSPECTION METHOD

CROSS-REFERENCE TO RELATED APPLICATION

This application claims the priority benefit of Taiwan application serial no. 92112090, filed May 2, 2003.

BACKGROUND OF THE INVENTION

1. Field of Invention

The present invention relates to a mask inspection method. More particularly, the present invention relates to a chrome-less mask inspection method.

2. Description of Related Art

In semiconductor fabrication, patterns are transferred through a set of masks. In other words, quality of the mask directly affects the pattern resulting from the transfer. Therefore, a newly fabricated mask must be inspected to ensure the mask is defect free before actual use.

In general, there are two mask inspection methods. One method is called the die-to-die inspection method. In the die-to-die inspection method, the patterns in neighboring units are compared to detect any discrepancies. Another method is called the die-to-database inspection method. In the die-to-database inspection method, the actual pattern is compared with the designed pattern. For the die-to-die inspection method, if the defects on two neighboring units are at the same location, the defects may not be found. On the other hand, since the design pattern is the basis for producing the mask, the design pattern is often verified with great care. Hence, the die-to-database inspection method has a much higher accuracy and is particularly suitable for conducting an initial mask inspection.

However, the die-to-database inspection method is unsuitable for inspecting a chrome-less mask. FIGS. 1A to 1C are a series of diagrams including a top view and sectional view of a conventional mask with a light-blocking pattern and a chrome-less phase shift pattern thereon and a signal trace after traversing the mask. In fact, FIG. 1A is a top view of a conventional mask with light-blocking pattern and chrome-less phase shift pattern thereon. FIG. 1B is a cross-sectional view along line 1B—1B of FIG. 1A. FIG. 1C is an inspection signal pattern after inspecting the mask by scanning along line 1B—1B. As shown in FIGS. 1A and 1B, the mask 100 includes, for example, a transparent region 110, a phase shift region 120 and a light-blocking region 130 on a transparent substrate 102. The transparent region 110 and the phase shift region 120 are formed, for example, by cutting up the transparent substrate 102 into separate blocks each with a different height. The light-blocking region 130 is formed, for example, by depositing chromium material on specific area of the transparent substrate 102 to form a chromium layer 104. As shown in FIG. 1C, a signal trace 150 of this chrome-less mask 100 has a corresponding down-spike 152 at the phase shift region 110 and the transparent region 120.

FIG. 2A shows a first mask database (the design pattern) 160 inside a built-in database for designing and fabricating the chrome-less mask 100. The first mask database 160 includes a phase shift region corresponding to the phase shift pattern 162 and a light-blocking region corresponding to the light-blocking pattern 164 for patterning out the transparent region 110, the phase shift region 120 and the light-blocking region 130 of the chrome-less mask 100. Using the first mask database 160, a mask with a cross-sectional structure as shown in FIG. 2B is produced. The mask has a chromium layer 104 over both the phase shift region 110 and the light-blocking region 130 of the transparent substrate 102. FIG. 2C shows an inspection signal pattern 170 generated by the first mask database 160.

FIG. 3A shows a second mask database 180 inside a built-in database for designing and fabricating the chrome-less mask 100. The second mask database 180 includes a light-blocking region corresponding to a light-blocking pattern 164 for removing the chromium layer 104 over the phase shift region 120. Using the second mask database 180, a mask with a cross-sectional structure as shown in FIG. 3B is produced. FIG. 3C shows an inspection signal pattern 190 generated by the second mask database 180.

A comparison of the signals 150, 170, 190 in FIGS. 1C, 2C and 3C shows that the actual inspection signal pattern 150 is different from inspection signal patterns 170, 190 generated by other designing patterns. In other words, signals generated by the designing pattern of databases do not reflect the signals produced by an actual chrome-less mask. That means, the die-to-database inspection method cannot be applied to detect defects in a chrome-less mask.

SUMMARY OF THE INVENTION

Accordingly, one object of the present invention is to provide a method of inspecting a chrome-less mask that uses a die-to-database inspection method to carry out the chrome-less mask inspection.

To achieve these and other advantages and in accordance with the purpose of the invention, as embodied and broadly described herein, the invention provides a chrome-less mask inspection method. The chrome-less mask at least includes a transparent region and a phase shift region. The method includes providing a database for holding a mask database that corresponds to the chrome-less mask. The mask database further includes a frame line pattern having enclosed area and pattern that corresponds to enclosed area and pattern of the phase shift region of the chrome-less mask and a first inspection signal pattern generated by the mask database. An inspecting device is also provided to inspect a second inspection signal pattern from the chrome-less mask. Furthermore, scanning location of the second inspection signal pattern corresponds with scanning location of the first inspection signal pattern. Thereafter, the first inspection signal pattern and the second inspection signal pattern is compared and any differences are registered. Identical first inspection signal pattern and second inspection signal pattern indicates a defect-free chrome-less mask.

Furthermore, in the aforementioned embodiment, the mask database is generated using a second mask database for designing the chrome-less mask. The second mask database includes a phase shift pattern. Area and pattern of this phase shift pattern corresponds with area and pattern of the phase shift region in the chrome-less mask. The aforementioned frame line pattern borders the phase shift pattern. In fact, the frame line pattern is adjacent to and encloses the phase shift pattern. Afterwards, the phase shift pattern is removed so that the frame line pattern is retained to form the mask database.

This invention uses the built-in mask database (design pattern) for designing and fabricating the chrome-less mask to generate a new mask database with inspection signal pattern identical to the one produced by a normally produced mask. The inspection signal pattern generated by the new mask database is stored inside the database. Hence, a database with the correct inspection signal pattern is built for conducting a die-to-database inspection of a chrome-less mask.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1A:
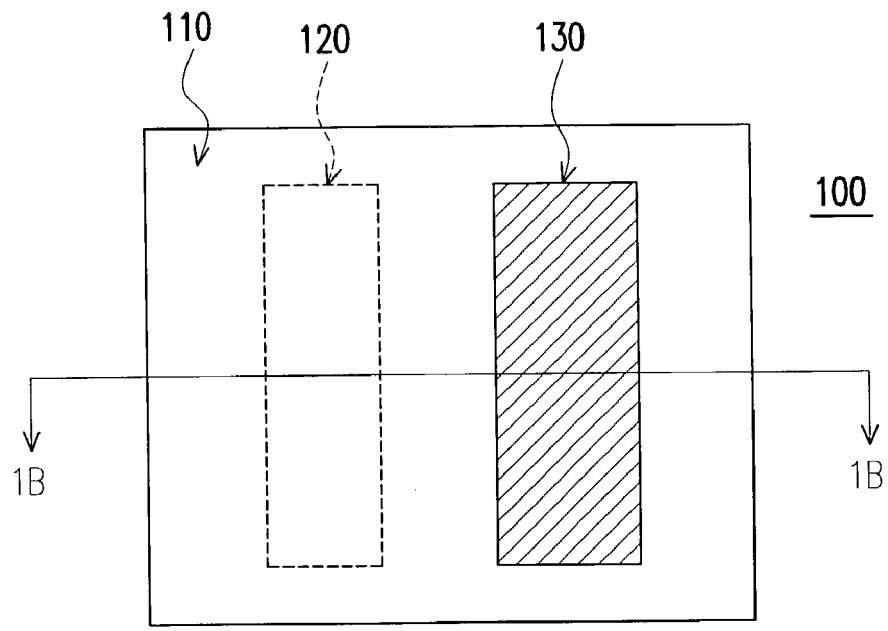
FIG. 1A is a top view of a conventional mask with light-blocking pattern and chrome-less phase shift pattern thereon.
Figure 1B:
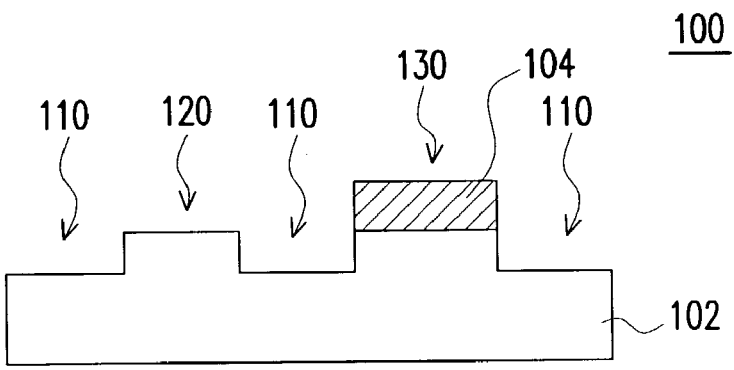
FIG. 1B is a cross-sectional view along line 1B—1B of FIG. 1A.
Figure 1C:
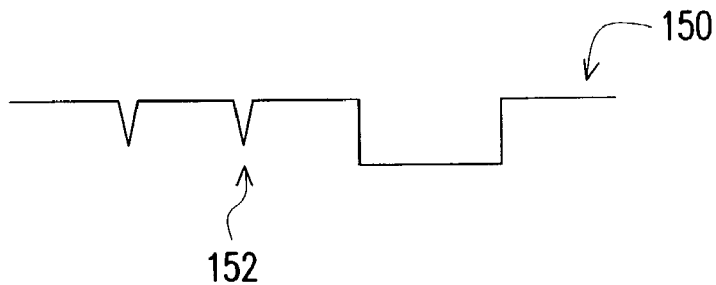
FIG. 1C is a signal trace after inspecting the mask by scanning along line 1B—1B.
Figure 2A:
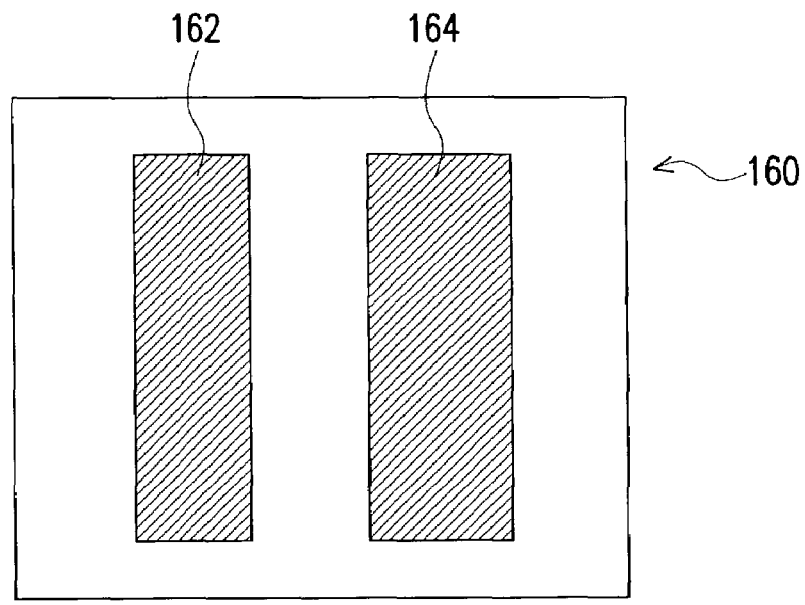
FIG. 2A shows a first mask database for designing and fabricating the chrome-less mask in FIG. 1A.
Figure 2B:
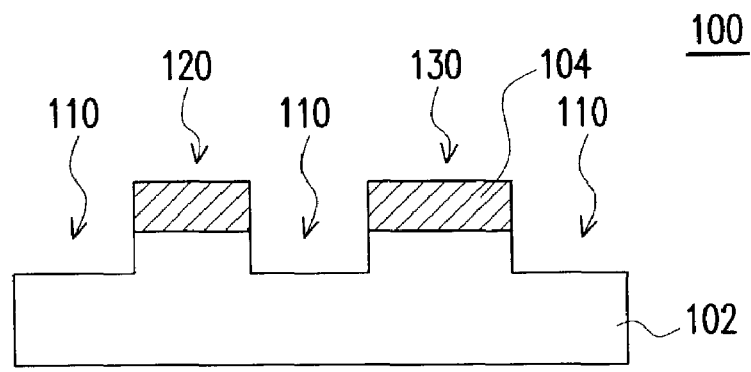
FIG. 2B is the cross-sectional view of a mask after conducting photolithographic and etching processes according to FIG. 2A.
Figure 2C:
FIG. 2C is an inspection signal pattern generated by the first mask database according to FIG. 2A.
Figure 3A:
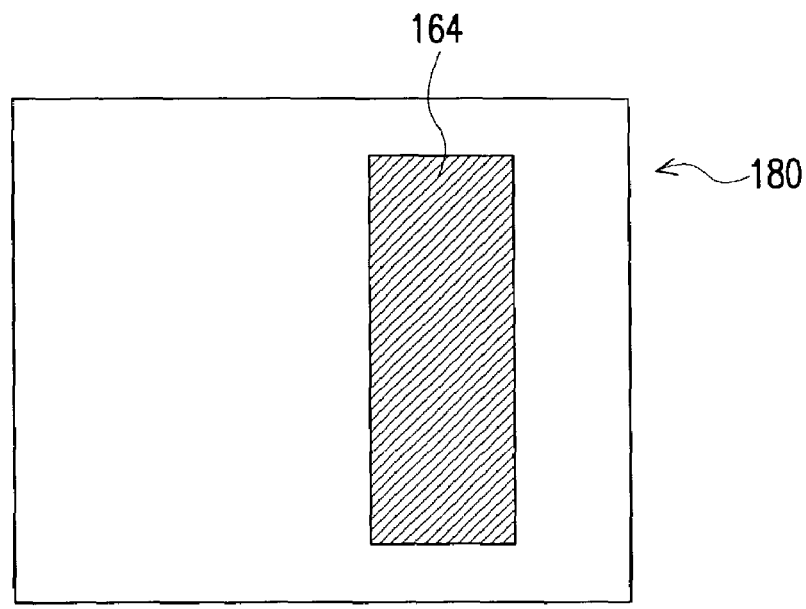
FIG. 3A shows a second mask database for designing and fabricating the chrome-less mask in FIG. 1A.
Figure 3B:
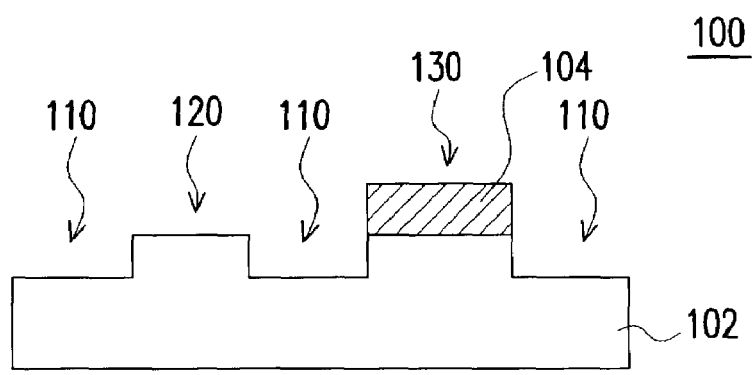
FIG. 3B is the cross-sectional view of a mask after conducting photolithographic and etching processes according to FIG. 3A.
Figure 3C:
FIG. 3C is an inspection signal pattern generated by the second mask database according to FIG. 3A.

Reference will now be made in detail to the present preferred embodiments of the invention, examples of which are illustrated in the accompanying drawings. Wherever possible, the same reference numbers are used in the drawings and the description to refer to the same or like parts.

In this invention, a new mask database with inspection signal pattern identical to the one produced by a normally produced mask is used for inspecting the mask. Hence, the new mask database must be built according to the mask database (design pattern) used for designing and fabricating the chrome-less mask.

Figure 4A:
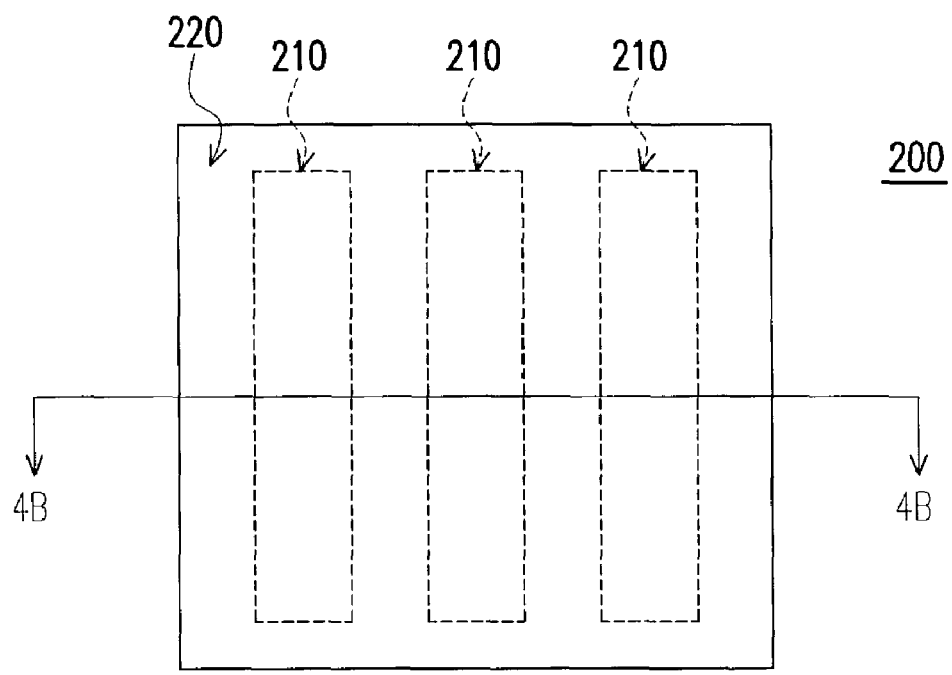
FIG. 4A is a top view of a mask according to a first preferred embodiment of this invention.
Figure 4B:
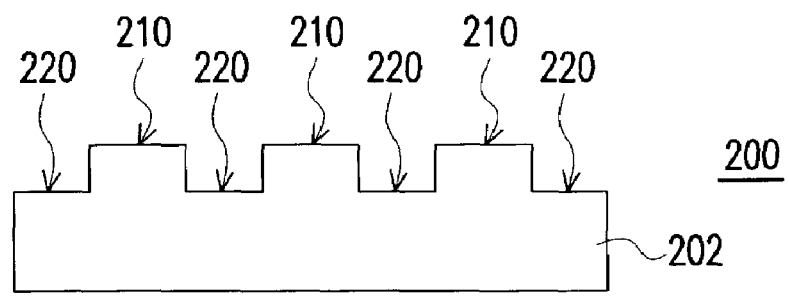
FIG. 4B is a cross-sectional view of the mask according to the first preferred embodiment of this invention.
Figure 4C:
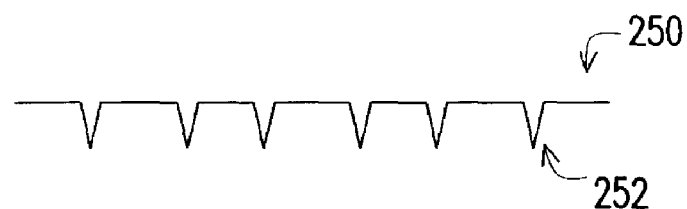
FIG. 4C shows an inspection signal pattern obtained in the process of inspecting the mask according to the first preferred embodiment of this invention.

A mask 200 comprising of chromium-less phase shift patterns is provided. FIG. 4A is a top view of the mask 200 according to a first preferred embodiment of this invention and FIG. 4B is a cross-sectional view along line 4B—4B of the mask. The mask 200 has at least a transparent region 210 and a phase shift region 220. The transparent region 210 and the phase shift region 220 are formed, for example, by cutting a transparent substrate 202 into blocks at different height level such that the transparent region 210 has a thickness greater than the phase shift region 220. The transparent substrate 202 (including the transparent region 210 and the phase shift region 220) is fabricated using a material including, for example, quartz. FIG. 4C shows an inspection signal pattern 250 obtained by scanning the chrome-less mask with an inspection tool along the sectional line 4B—4B. The inspection signal pattern 250 has a downspike 252 at all step edges between the transparent region 210 and the phase shift region 220.

Figure 5:
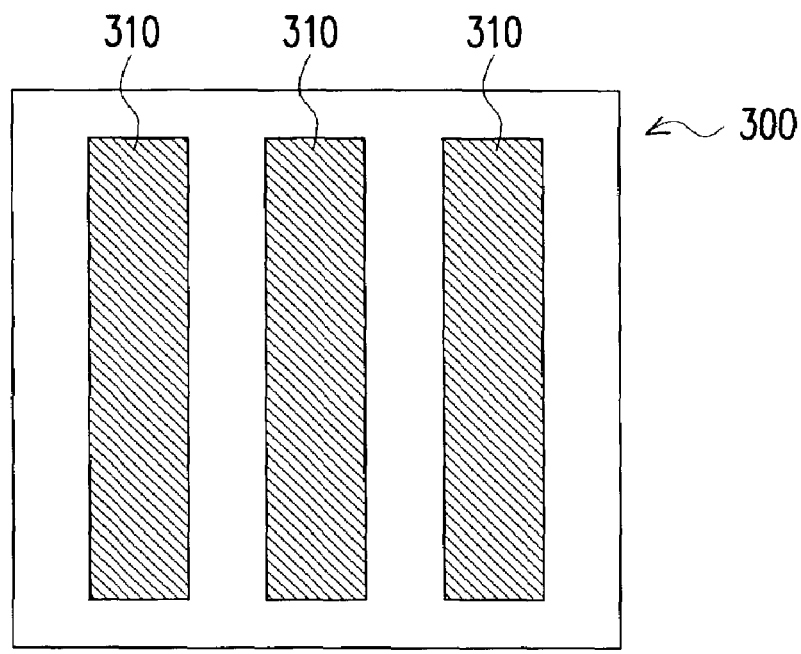
FIGS. 5 to 7 are diagrams showing the mask databases for producing an inspection signal identical to the signal produced by a mask according to the first preferred embodiment of this invention.

FIG. 5 is a diagram showing a mask database (design pattern) 300 inside the database for designing and fabricating the mask 200. The mask database 300 is a CAD pattern, for example. As shown in FIG. 5, the mask database 300 includes a phase shift pattern 310 that correspond to the phase shift region 220 in the mask 200. In the fabrication of the mask 200, the phase shift pattern 310 is transferred as a chromium layer (not shown) over the transparent substrate according to the mask database 300. Thereafter, the transparent substrate is etched to form the transparent region and the phase shift region.

Figure 6:
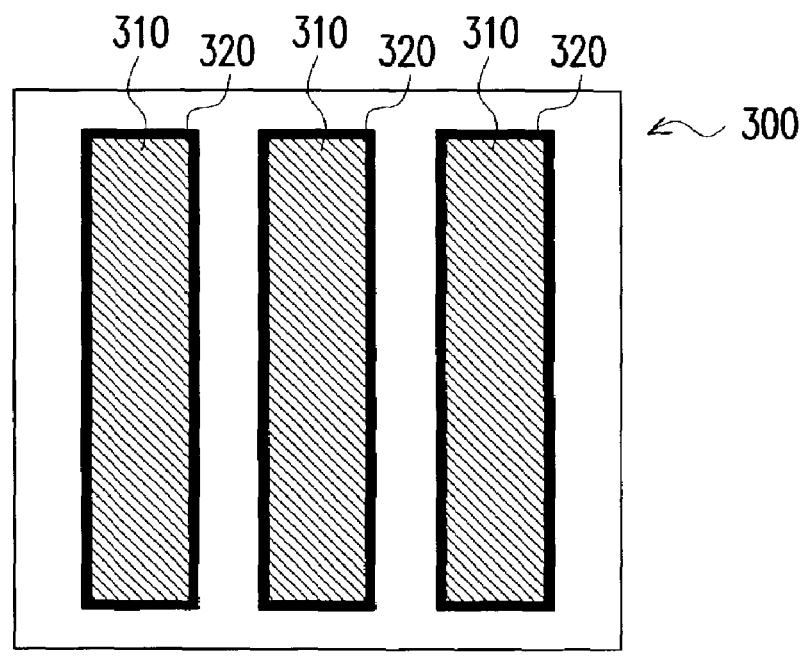
Figure 7:
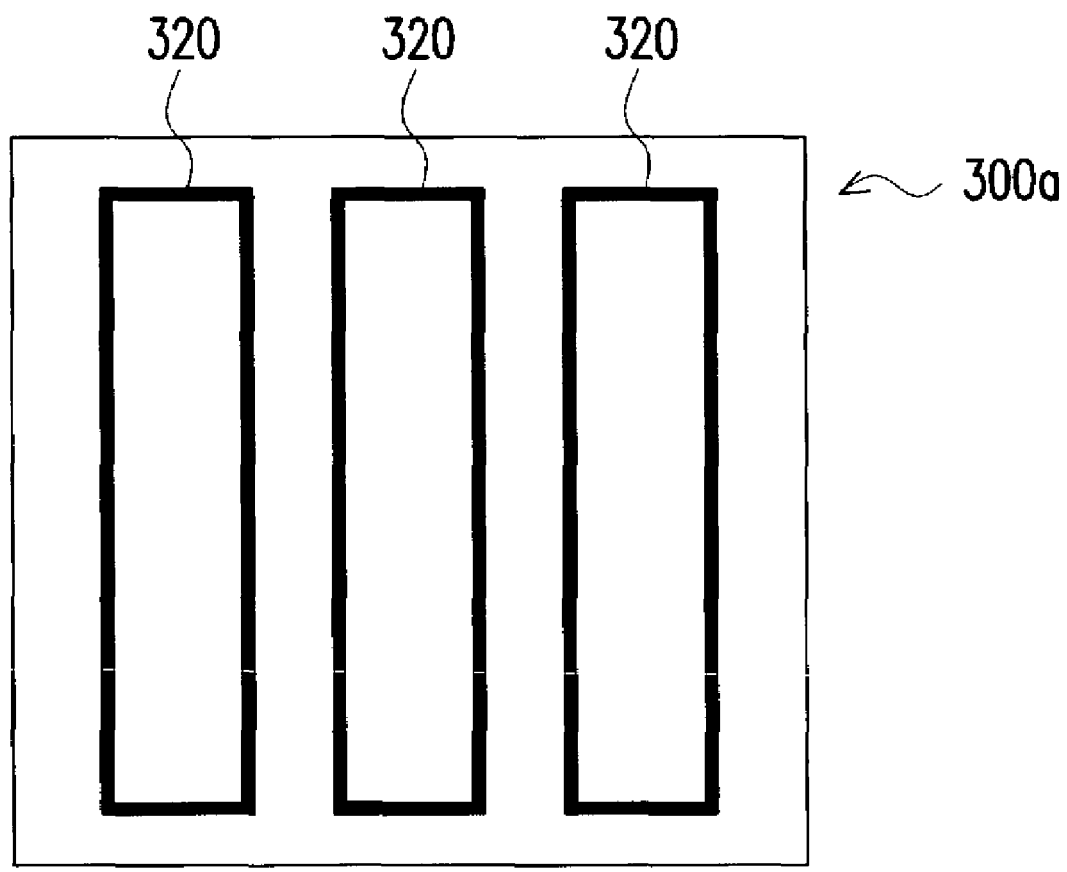

As shown in FIG. 6, using the mask database 300 as a base, a frame line pattern 320 is established within the mask database 300. The frame line pattern 320 is laid on the outer edge of the phase shift pattern 310 surrounding the phase shift pattern 310 entirely. Next, as shown in FIG. 7, the phase shift pattern 310 is removed from the mask database 300. At this stage, the mask database 300 inside the database is transformed to a mask database 300a comprising of the frame line pattern 320. Thus, the area and pattern enclosed by the frame line pattern 320 corresponds with the area and pattern enclosed by the phase shift region 220 of the mask 200.

Figure 8:
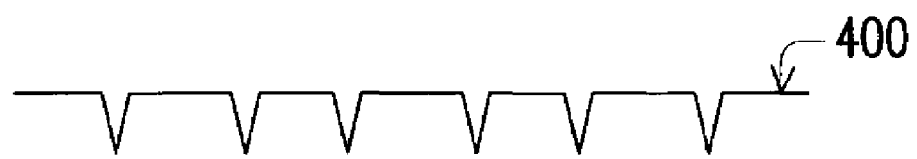
FIG. 8 shows an inspection signal pattern generated by the mask database in FIG. 7.

FIG. 8 shows an inspection signal pattern 400 corresponding to the mask database 300a. The scanning location of the inspection signal 400 corresponds with the scanning location of the inspection signal 250. Furthermore, the inspection signal 400 is obtained according to the mask database 300a after suitable transformation/calculation using software and then stored inside the database. Because a centrally hollow frame line pattern 320 is formed within the mask database 300a, the inspection signal pattern 400 will be identical to the actual inspection signal pattern 250 of the mask 200 shown in FIG. 4C.

Through database processing of the mask database 300 laid out in FIGS. 5 to 7 to establish a new mask database 300a, an inspection signal pattern 400 identical to the actual inspection signal pattern 250 of the mask 200 is obtained. Consequently, a die-to-database inspection of the chrome-less mask is possible.

Figure 9A:
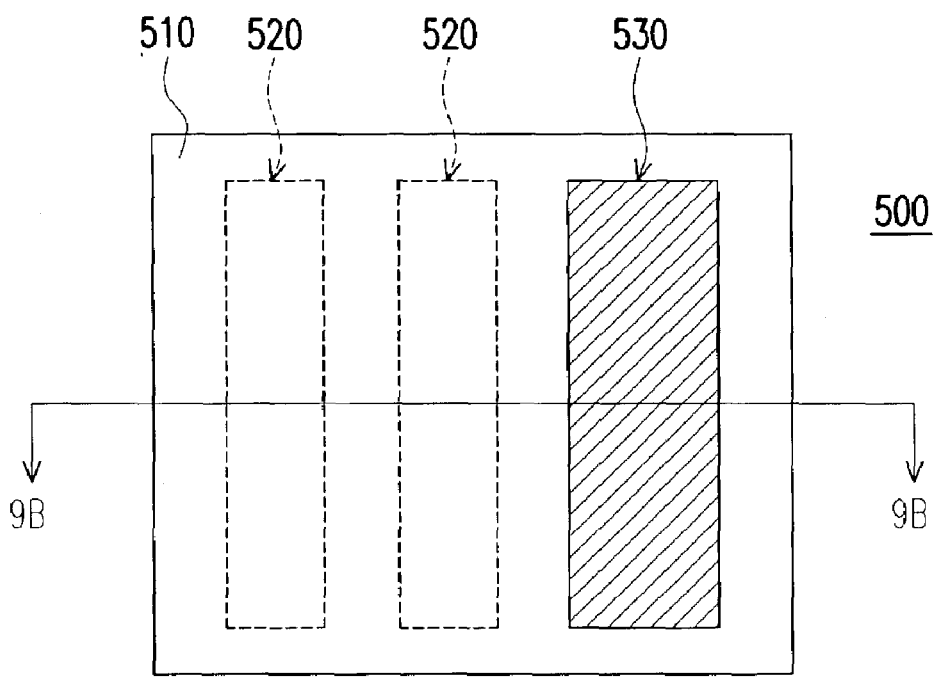
FIG. 9A is a top view of a mask according to a second preferred embodiment of this invention.
Figure 9B:
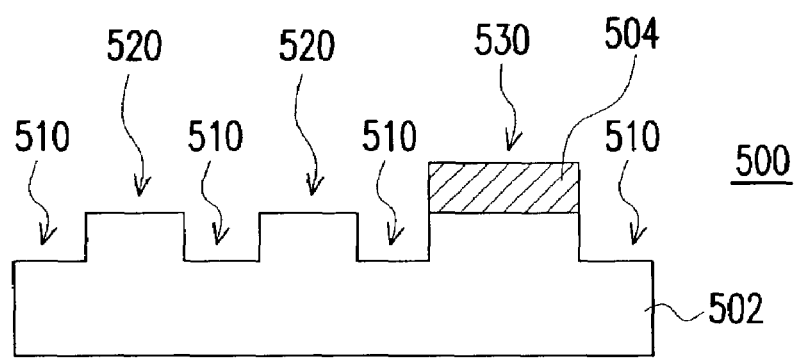
FIG. 9B is a cross-sectional view of the mask according to the second preferred embodiment of this is invention.
Figure 9C:
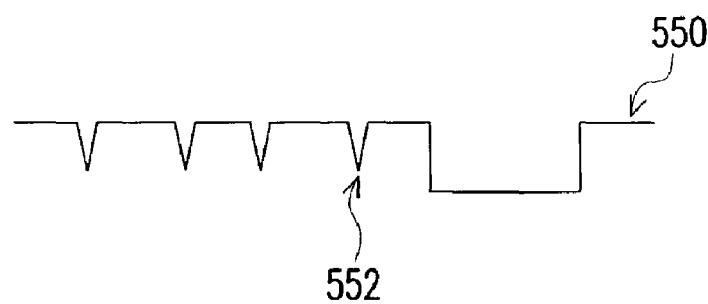
FIG. 9C shows an inspection signal pattern obtained in the process of inspecting the mask according to the second embodiment of this invention.

In another embodiment of this invention, a mask 500 comprising of a mixture of chromium-less phase shift patterns and light-blocking patterns is provided. FIG. 9A is a top view of the mask 500 according to a second preferred embodiment of this invention and FIG. 9B is a cross-sectional view along line 9B—9B of the mask 500. The mask 500 has at least a transparent region 510, a phase shift region 520 and a light-blocking region 530. The transparent region 510 and the phase shift region 520 are formed, for example, by cutting a transparent substrate 502 into blocks at different height level such that the transparent region 510 has a thickness greater than the phase shift region 520. The light-blocking region 530 is formed, for example, by depositing light-blocking material on specified regions of the transparent substrate 502 to form a light-blocking layer 504. The transparent substrate 502 (including the transparent region 510 and the phase shift region 520) is fabricated using a material including, for example, quartz. The light-blocking layer 504 is fabricated using a material including, for example, chromium. FIG. 9C shows an inspection signal pattern 550 obtained by scanning the chrome-less mask with an inspection tool along the sectional line 9B—9B. The inspection signal pattern 550 has a down-spike 552 at all step edges between the transparent region 510 and the phase shift region 520.

Figure 10:
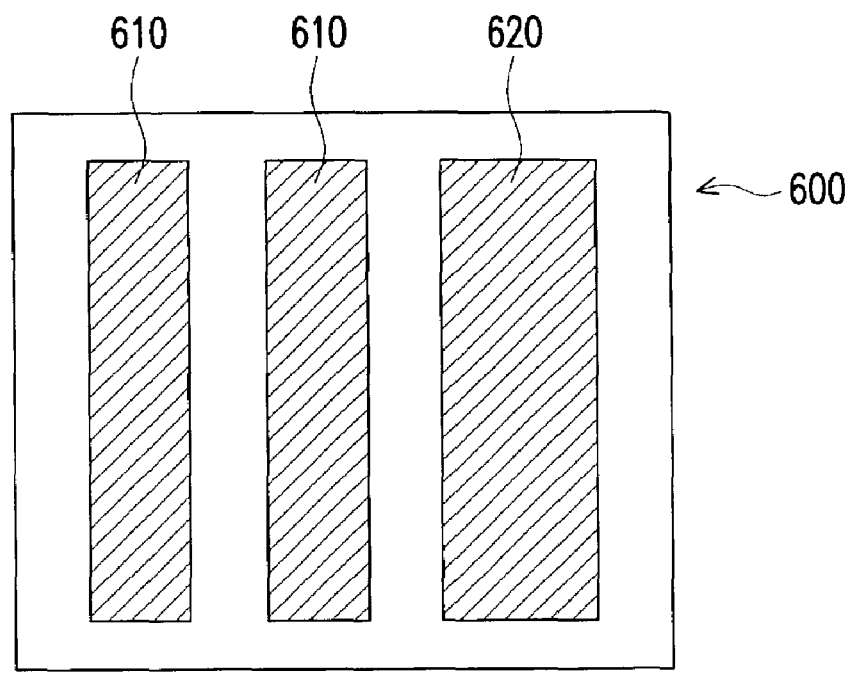
FIGS. 10 to 13 are diagrams showing the mask databases for producing an inspection signal identical to the signal produced by a mask according to the second preferred embodiment of this invention.

FIG. 10 is a diagram showing a mask database (design pattern) 600 inside the database for designing and fabricating the mask 500. The mask database 600 is a CAD pattern, for example. As shown in FIG. 10, the mask database 600 includes a phase shift pattern 510 that correspond to the phase shift region 520 in the mask 200 and a light-blocking pattern 620 that corresponds to the light-blocking region 530. In the fabrication of the mask 500, the mask database 600 is applied to transfer a phase shift pattern 610 and a light-blocking pattern 620 to a light-blocking layer (not shown) on the transparent substrate. Thereafter, the transparent substrate is etched to form transparent regions as well as light-blocking layer covered phase shift regions and light-blocking regions.

Figure 11:
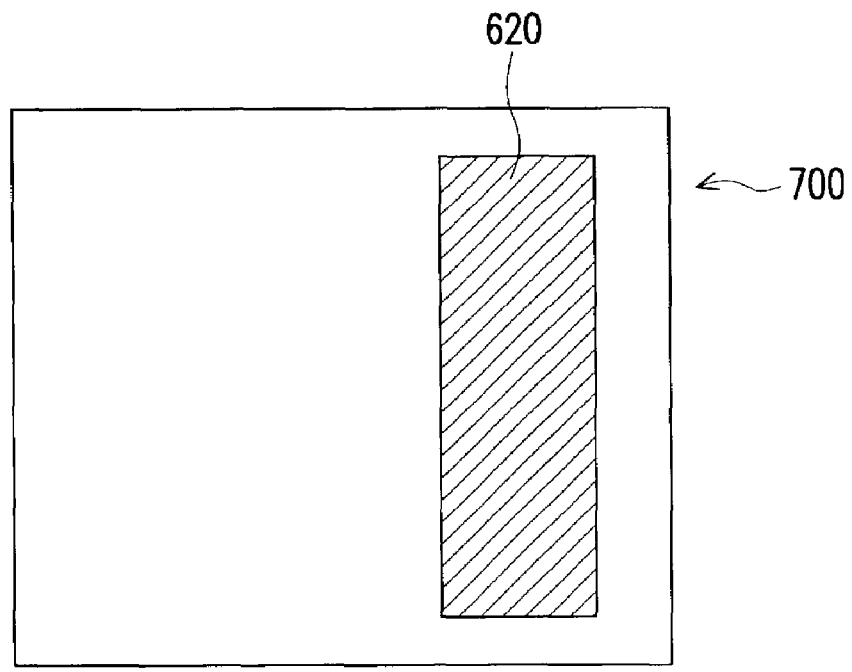

FIG. 11 is a diagram showing a mask database (design pattern) 700 inside the database for designing and fabricating the mask 500. The mask database 700 is a CAD pattern, for example. As shown in FIG. 11, the mask database 700 is the mask database 600 after removing the phase shift patterns 610. Hence, the mask database 700 includes the light-blocking pattern 620 that corresponds with the light-blocking region 530 of the mask 500. In the fabrication of the mask 500, the mask database 700 is applied to remove the chromium layer outside the light-blocking region 530 to produce a mask having both chrome-less phase shift patterns and light-blocking patterns.

Figure 12:
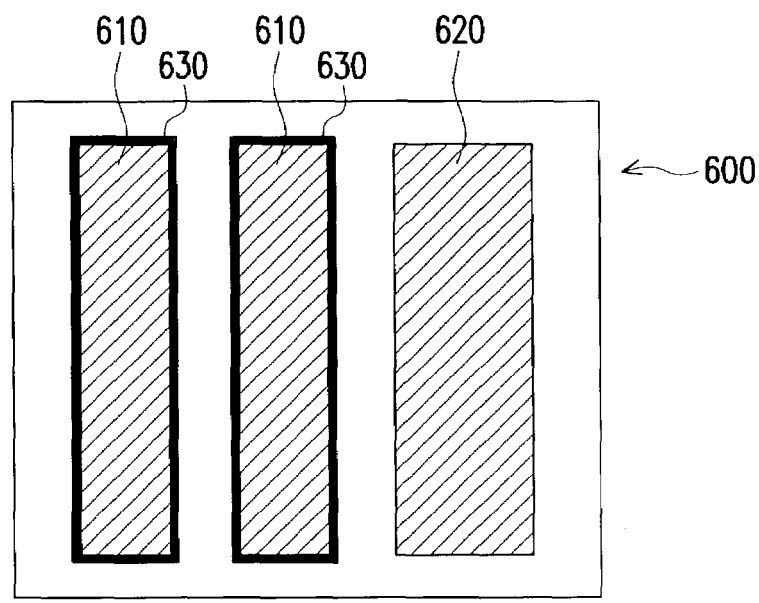
Figure 13:
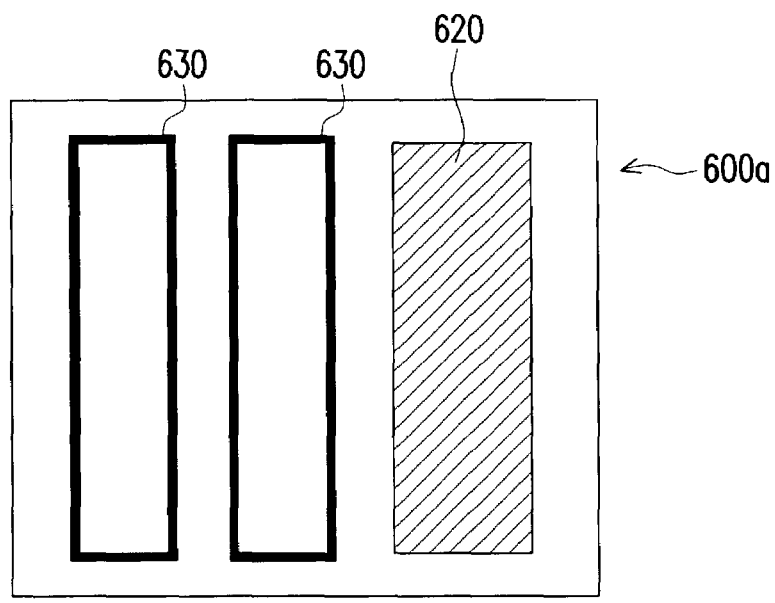

As shown in FIG. 12, using the mask database 600 as a base, a frame line pattern 630 is established within the mask database 600. The frame line pattern 630 is laid on the outer edge of the phase shift pattern 610 surrounding the phase shift pattern 610 entirely. Next, as shown in FIG. 13, the phase shift pattern 610 corresponding to the phase shift regions 520 of the mask 500 is removed from the mask database 600. At this stage, the mask database 600 inside the database is transformed to a mask database 600a comprising of the frame line pattern 630 and the light-blocking patterns 620. Furthermore, the area and pattern enclosed by the frame line pattern 630 corresponds with the area and pattern enclosed by the phase shift region 220 of the mask 200.

Figure 14:
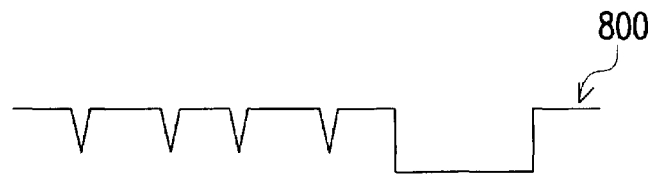
FIG. 14 shows an inspection signal pattern generated by the mask database in FIG. 13.

FIG. 14 shows an inspection signal pattern 800 corresponding to the mask database 600a. The scanning location of the inspection signal 800 corresponds with the scanning location of the inspection signal 550. Furthermore, the inspection signal 800 can be obtained according to the mask database 600a after suitable transformation/calculation using software and then stored inside the database. Because a centrally hollow frame line pattern 630 is formed within the mask database 600a, the inspection signal pattern 800 will be identical to the actual inspection signal pattern 550 of the mask 500 shown in FIG. 9C.

Through database processing of the mask database 600 laid out in FIGS. 9 to 13 to establish a new mask database 600a, an inspection signal pattern 800 identical to the actual inspection signal pattern 550 of the mask 500 is obtained. Consequently, a die-to-database inspection of the chrome-less mask having chrome-less phase shift patterns and light-blocking patterns thereon is possible.

In the aforementioned first and second embodiments of this invention, inspection signal pattern for each location can be established using the aforementioned methods. Hence, the inspection signal patterns for inspecting the entire mask can be built within a mask database so that an inspection tool may utilize the database to carry out a complete die-to-database inspection and find any defects on a mask.

In addition, there is not particular restriction on the width of a frame line pattern in this invention. Width of the frame line pattern may be adjusted according to the actual inspection signals produced by the inspecting instrument so that the inspection signal pattern embodied within the database and the actual inspection pattern are identical.

In the first and the second embodiment of this invention, a new mask database is built according to the mask database (design pattern) for designing and fabricating the chrome-less mask so that the inspection signal pattern is identical to the one produced by a normally produced mask. In the following third embodiment of this invention, a method of using a database with the new mask database and corresponding inspection signal pattern to inspect a chrome-less mask is described.

Figure 15:
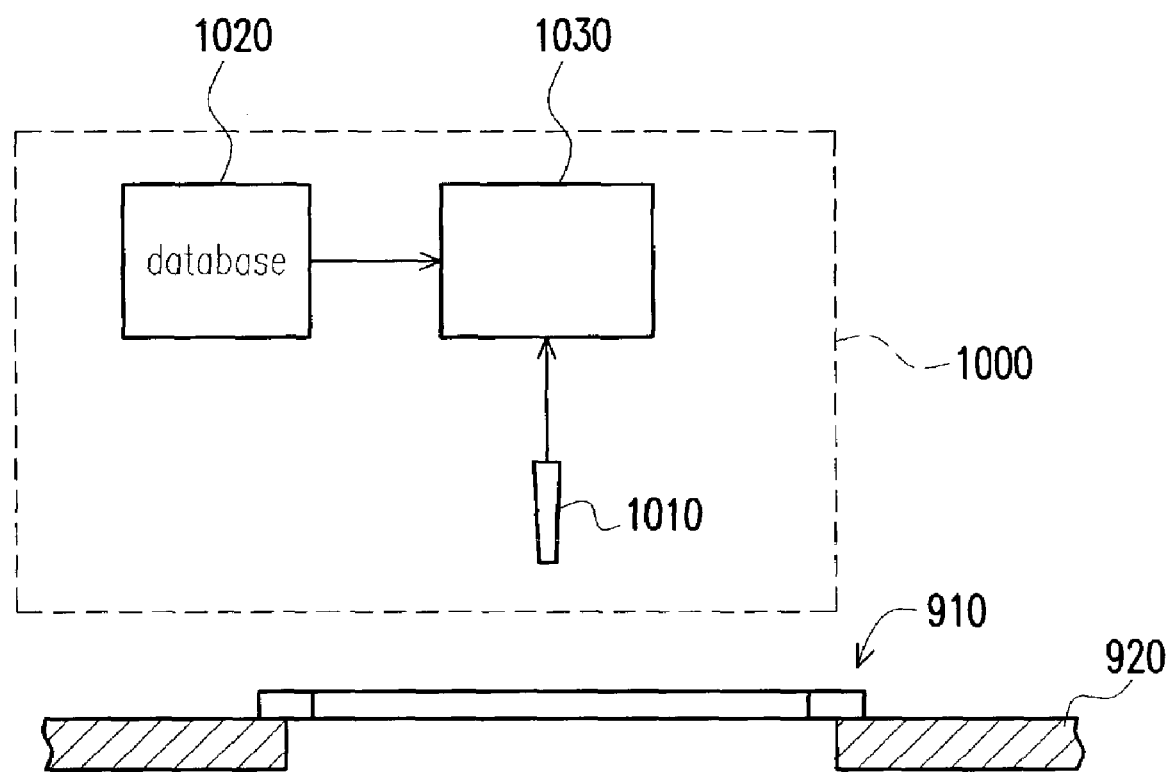
FIG. 15 is a diagram showing the inspection of a chrome-less mask using a die-to-database inspection method according to the embodiment of this invention.

FIG. 15 is a diagram showing the inspection of a chrome-less mask using a die-to-database inspection method according to the embodiment of this invention. As shown in FIG. 15, a mask 910 is placed on a mask holder 920. The mask 910 is, for example, a chrome-less mask containing transparent regions and phase shift regions only as in the first embodiment or a mixed chrome-less mask containing chrome-less phase shift patterns and light-blocking patterns. An inspection instrument 1000 is provided. The inspection instrument 1000 at least includes an inspection probe 1010 for inspecting the mask 910 and obtaining an actual inspection signal pattern, a database 1020 for holding mask databases and inspection signal patterns obtained through the first or the second embodiment, a processing unit 1030 connected both to the inspection probe 1010 and the database 1020 for comparing the actual inspection signal pattern with database-generated pattern. By feeding the actual inspection signals obtained from the inspection probe 1010 and the database-generated signals into the processor unit 1030, a die-to-database comparison can be carried out. In addition, both the inspection probe 1010 and he mask 910 are movable so that the entire mask 910 can be scanned so that a die-to-database inspection of the entire mask 910 is possible.

In summary, this invention uses a built-in mask database (design pattern) for designing and fabricating a chrome-less mask to generate a new mask database with inspection signal pattern identical to the one produced by a normally produced mask. The inspection signal pattern generated by the new mask database is stored inside the database so that a correct inspection signal pattern can be produce to conduct a die-to-database inspection of a chrome-less mask whenever necessary.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for inspecting a chrome-less mask, wherein the chrome-less mask at least includes a transparent region and a phase shift region, the method comprising the steps of:
   providing a database holding:
      a mask database that corresponds to the chrome-less mask, wherein the mask database includes a frame line pattern and that area and pattern enclosed by the frame line pattern corresponds with area and pattern enclosed by the phase shift region of the chrome-less mask; and
      a first inspection signal pattern, wherein the first inspection signal pattern is generated by the mask database;
   providing an inspection instrument for inspecting the chrome-less mask and a second inspection signal pattern for inspecting the chrome-less mask, wherein scanning location of the second inspection signal pattern corresponds to scanning location of the first inspection signal pattern; and
   comparing the first inspection signal with the second inspection signal to find any difference, wherein no discrepancies between the first inspection signal pattern and the second inspection signal pattern indicates the chrome-less mask is defect-free.

2. The inspection method of claim 1, wherein material forming the transparent region includes quartz.

3. The inspection method of claim 1, wherein material forming the phase shift region includes quartz.

4. The inspection method of claim 1, wherein the phase shift region has a thickness greater than the transparent region.

5. The inspection method of claim 1, wherein the chrome-less mask further includes a light-blocking region.

6. A method of inspecting a chrome-less mask, wherein the chrome-less mask at least includes a transparent region and a phase shift region, the method comprising the steps of:
   providing a database holding:
      a first mask database corresponding to the chrome-less mask, wherein the first mask database further includes a phase shift pattern and that area and pattern of the phase shift pattern corresponds with area and pattern of the chrome-less mask;
      a second mask database, wherein the second mask database further includes a frame line pattern and that area and pattern of the frame line pattern is identical to the area and pattern of the phase shift pattern of the first mask database; and
      a first inspection signal pattern, wherein the first inspection signal pattern is generated by the second mask database;
   providing an inspection instrument for inspecting the chrome-less mask and a second inspection signal pattern for inspecting the chrome-less mask, wherein the scanning location of the second inspection signal pattern corresponds to the scanning location of the first inspection signal pattern; and
   comparing the first inspection signal with the second inspection signal to find any difference, wherein no discrepancies between the first inspection signal pattern and the second inspection signal pattern indicates the chrome-less mask is defect-free.

7. The inspection method of claim 6, wherein material forming the transparent region includes quartz.

8. The inspection method of claim 6, wherein material forming the phase shift region includes quartz.

9. The inspection method of claim 6, wherein the phase shift region has a thickness greater than the transparent region.

10. The inspection method of claim 6, wherein the chrome-less mask further includes a light-blocking region.

11. The inspection method of claim 6, wherein the first mask database is used for designing the chrome-less mask.

12. The inspection method of claim 6, wherein producing the second mask database includes the sub-steps of:
   forming frame line pattern just outside the phase shift pattern of the first mask database and surrounding the phase shift pattern entirely; and
   removing the phase shift pattern from the first mask database so that the frame line pattern is retained to form the second mask database.

* * * * *